(12) United States Patent
Xu (10) Patent No.: US 8,896,804 B2
(45) Date of Patent: Nov. 25, 2014

(54) METHOD AND DEVICE FOR TERMINATION DETECTION OF OPTICAL ALIGNMENT OF LIQUID CRYSTAL MATERIAL

(71) Applicant: Shenzhen China Star Optoelectronics Technology Co., Ltd., Shenzhen, Guangdong (CN)

(72) Inventor: Liang Xu, Shenzhen (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 228 days.

(21) Appl. No.: 13/702,612

(22) PCT Filed: Nov. 27, 2012

(86) PCT No.: PCT/CN2012/085374
§ 371 (c)(1),
(2), (4) Date: Dec. 7, 2012

(87) PCT Pub. No.: WO2014/075351
PCT Pub. Date: May 22, 2014

(65) Prior Publication Data
US 2014/0139800 A1    May 22, 2014

(30) Foreign Application Priority Data
Nov. 19, 2012  (CN) .......................... 2012 1 0467331

(51) Int. Cl.
| G02F 1/1333 | (2006.01) |
| C09K 19/02  | (2006.01) |
| G05B 1/00   | (2006.01) |
| G05D 9/00   | (2006.01) |
| B01J 19/00  | (2006.01) |
| G01N 3/28   | (2006.01) |
| G02F 1/1337 | (2006.01) |
| G02F 1/13   | (2006.01) |

(52) U.S. Cl.
CPC ........ *G02F 1/133788* (2013.01); *G02F 1/1303* (2013.01)
USPC ................. 349/191; 349/86; 349/87; 349/88; 349/89; 349/90; 349/91; 349/92; 349/93; 349/183; 349/184; 422/105; 422/106; 422/107; 422/108

(58) Field of Classification Search
USPC ............................ 349/86–93, 183–186, 191; 422/105–108
See application file for complete search history.

(56) References Cited

U.S. PATENT DOCUMENTS

| 5,571,448 A      | * | 11/1996 | Wartenberg et al. | ........ 252/299.5 |
| 2005/0264737 A1  | * | 12/2005 | Kataoka et al.    | ................ 349/124 |
| 2013/0094084 A1  | * | 4/2013  | Merrill et al.    | ............ 359/485.03 |

* cited by examiner

*Primary Examiner* — Hoan C Nguyen
(74) *Attorney, Agent, or Firm* — Andrew C. Cheng (57) ABSTRACT

The present invention provides a method for termination detection of optical alignment of liquid crystal material, which includes: under influence of electrical field, irradiating light on liquid crystal material so that reactive monomers in liquid crystal material polymerizing; detecting a residual amount or a thickness change value of the reactive monomers in liquid crystal material to determine detected residual amount of reactive monomers or thickness change value in liquid crystal box reaching a default value; when reaching default value, terminating optical alignment of liquid crystal material. The present invention also provides a device for termination detection of optical alignment of liquid crystal material. Through detecting termination of optical alignment, the present invention realizes automatic control of irradiation time in optical alignment to reduce the effect of individual glass substrate variation on optical alignment to avoid affecting reaction process of alignment on reactive monomer.

17 Claims, 5 Drawing Sheets

METHOD AND DEVICE FOR TERMINATION DETECTION OF OPTICAL ALIGNMENT OF LIQUID CRYSTAL MATERIAL

The present application claims priority of "METHOD AND DEVICE FOR TERMINATION DETECTION OF OPTICAL ALIGNMENT OF LIQUID CRYSTAL MATERIAL", application number 201210467331.7 submitted to State Intellectual Property Office, People Republic of China dated Nov. 19, 2012.

BACKGROUND OF THE INVENTION

1. Field of the Invention

The present invention relates to the field of liquid crystal displaying techniques, and in particular to a method and device for termination detection of optical alignment of liquid crystal material.

2. The Related Arts

As the information era progresses, the demand on display device increases. To meet the demand, many panel display device are rapidly developed, such as, liquid crystal display device (LCD), plasma display panel (PDP), and organic light-emitting diode (OLED).

Among the panel displays, the LCD is gradually replacing the cold cathode display device due to the advantages of light weight, small size and low energy-consumption. However, the early twisted nematic (TN) or super twisted nematic (STN) LCDs all have the problems of low contrast and poor view angle. As the demand on the display quality gets higher, the wide view angle displaying technique, such as, In Plan Switch (IPS), Vertically Alignment (VA), are gaining momentum in development.

IPS possesses good wide view angle displaying result. However, for better IPS display result, the demand on the friction process during manufacturing is also very high, which reduces the redundancy of the friction process, in particular, in mass production. Compared to IPS, VA wide view angle displaying technique does not require friction process during manufacturing, which shows certain competitive advantage.

At present, the liquid crystal doped with polymer monomer is often used. In subsequent process, through the double effect of the UV and electricity to realize optical alignment. This technique is called polymer stained vertical alignment (PSVA). The advantage of PSVA is that the result neither protrudes nor causes ITO slit on the color film side, which saves the cost of color film as well as improve the overall transmittance.

However, because the PSVA uses UV for alignment and UV radiates on the liquid crystal after passing layers of glass substrate and alignment film, the actual UV illumination on the liquid crystal is greatly affected by the substrate. During manufacturing, the control is achieved through controlling the time. However, in mass production, the individual substrate may vary, which renders the pure time control ineffectiveness due to insufficient or over alignment.

SUMMARY OF THE INVENTION

The technical issue to be addressed by the present invention is to provide a method and device for termination detection of optical alignment of liquid crystal material, through detecting the termination of the optical alignment to control the reaction termination. The present invention can reduce the effect of individual glass substrate variation on the optical alignment so as to avoid affecting the reaction process of alignment on reactive monomer.

The present invention provides a method for termination detection of optical alignment of liquid crystal material, which comprises: performing optical alignment on a liquid crystal material, which further comprising: under the influence of electrical field, irradiating light on the liquid crystal material so that reactive monomers in the liquid crystal material polymerizing; detecting a residual amount or a thickness change value of the reactive monomers in the liquid crystal material to determine the detected residual amount of the reactive monomers or thickness change value in the liquid crystal box reaching a default value; when reaching the default value, terminating optical alignment of the liquid crystal material.

According to a preferred embodiment of the present invention, the step of detecting a residual amount of the reactive monomers in the liquid crystal material further comprises: irradiating infrared light on the liquid crystal material; and based on the infrared absorption of the reactive monomers in the liquid crystal material, obtaining a density reduction in cinnamic acid in the reactive monomers.

According to a preferred embodiment of the present invention, the step of irradiating infrared light on the liquid crystal material further comprises: irradiating infrared light that will not cause the reactive monomers to polymerize on the liquid crystal material.

According to a preferred embodiment of the present invention, the step of based on the infrared absorption of the reactive monomers in the liquid crystal material, obtaining a density reduction in cinnamic acid in the reactive monomers further comprises: obtaining an absorption intensity of infrared light of specific wavelength by carbon-carbon double bond in cinnamic acid.

According to a preferred embodiment of the present invention, the step of irradiating infrared light on the liquid crystal material further comprises: irradiating infrared light that will not cause the reactive monomers to polymerize on the liquid crystal material.

According to a preferred embodiment of the present invention, the step of detecting a thickness change value in the liquid crystal box further comprises: irradiating an incident light that will not cause the reactive monomers to polymerize on the liquid crystal material.

According to a preferred embodiment of the present invention, the incident light has a wavelength of 580 nm.

The present invention provides a device for termination detection of optical alignment of liquid crystal material, which comprises: an electrical field device for generating an electrical field; an irradiation device for irradiating light so as to cause reactive monomers in a liquid crystal material to polymerize under the influence of electrical field and the irradiating light to realize optical alignment of liquid crystal material; a first detection device for detecting a residual amount of reactive monomers in the liquid crystal material; and a first determination device for determining whether the detected residual amount of reactive monomers in the liquid crystal material reaching a default value; wherein when the first determination device determining the default value being reached, terminating the optical alignment on the liquid crystal material.

According to a preferred embodiment of the present invention, the first detection device at least comprises: an infrared transmission probe, disposed at top of a box containing the liquid crystal material to irradiate infrared light on the liquid crystal box; an infrared receiving probe, disposed at bottom of the box containing the liquid crystal material to receive infrared light on the liquid crystal box; and a density detector, based on conditions of the infrared transmission probe irradiating infrared light and the infrared receiving probe receiving infrared light, for obtaining the infrared absorption intensity by the reactive monomers in the liquid crystal box and determining a reduction in a density of cinnamic acid in the reactive monomers.

According to a preferred embodiment of the present invention, the infrared transmission probe irradiates an infrared light that will not cause the reactive monomers to polymerize on the liquid crystal material.

According to a preferred embodiment of the present invention, the density detector, through obtaining an absorption intensity of infrared light of specific wavelength by carbon-carbon double bond in cinnamic acid, computes the residual amount of reactive monomers in the liquid crystal box.

According to a preferred embodiment of the present invention, the infrared transmission probe irradiates an infrared light that will not cause the reactive monomers to polymerize on the liquid crystal material.

The present invention provides a device for termination detection of optical alignment of liquid crystal material, which comprises: an electrical field device for generating an electrical field; an irradiation device for irradiating light so as to cause reactive monomers in a liquid crystal material to polymerize under the influence of electrical field and the irradiating light to realize optical alignment of liquid crystal material; a second detection device for detecting a thickness change value in a liquid crystal box of the liquid crystal material; and a second determination device for determining whether the detected thickness change value in the liquid crystal box reaching a default value; wherein when the second determination device determining the default value being reached, terminating the optical alignment on the liquid crystal material.

According to a preferred embodiment of the present invention, the second detection device at least comprises: a light source, for generating an incident light not causing the reactive monomers to polymerize to irradiate on the liquid crystal box.

According to a preferred embodiment of the present invention, the light source uses a visible light of wavelength 580 nm.

According to a preferred embodiment of the present invention, the second detection device further comprises: a polarizer disposed at the top of the liquid crystal box.

According to a preferred embodiment of the present invention, the second detection device further comprises: an analyzer disposed at the bottom of the liquid crystal box.

The efficacy of the present invention is that to be distinguished from the state of the art. Through detecting the residual amount of the reactive monomers or the thickness change in liquid crystal box, the present invention can determine the termination of the optical alignment on the liquid crystal material. As such, the present invention can realize the automatic control of the irradiation time in optical alignment to reduce the effect of individual glass substrate variation on the optical alignment to avoid affecting the reaction process of alignment on reactive monomer.

BRIEF DESCRIPTION OF THE DRAWINGS

To make the technical solution of the embodiments according to the present invention, a brief description of the drawings that are necessary for the illustration of the embodiments will be given as follows. Apparently, the drawings described below show only example embodiments of the present invention and for those having ordinary skills in the art, other drawings may be easily obtained from these drawings without paying any creative effort. In the drawings.

DETAILED DESCRIPTION OF THE PREFERRED EMBODIMENTS

The following refers to drawings to describe the preferred embodiment of the present invention.

Figure 1:
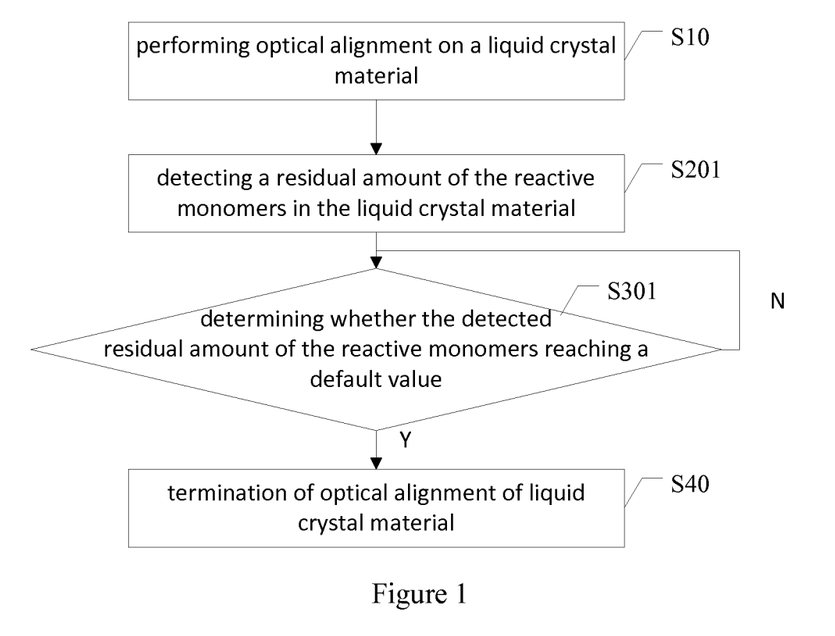
FIG. 1 is a flowchart showing the first embodiment of the method for termination detection of optical alignment of liquid crystal material according to the present invention.
Figure 2:
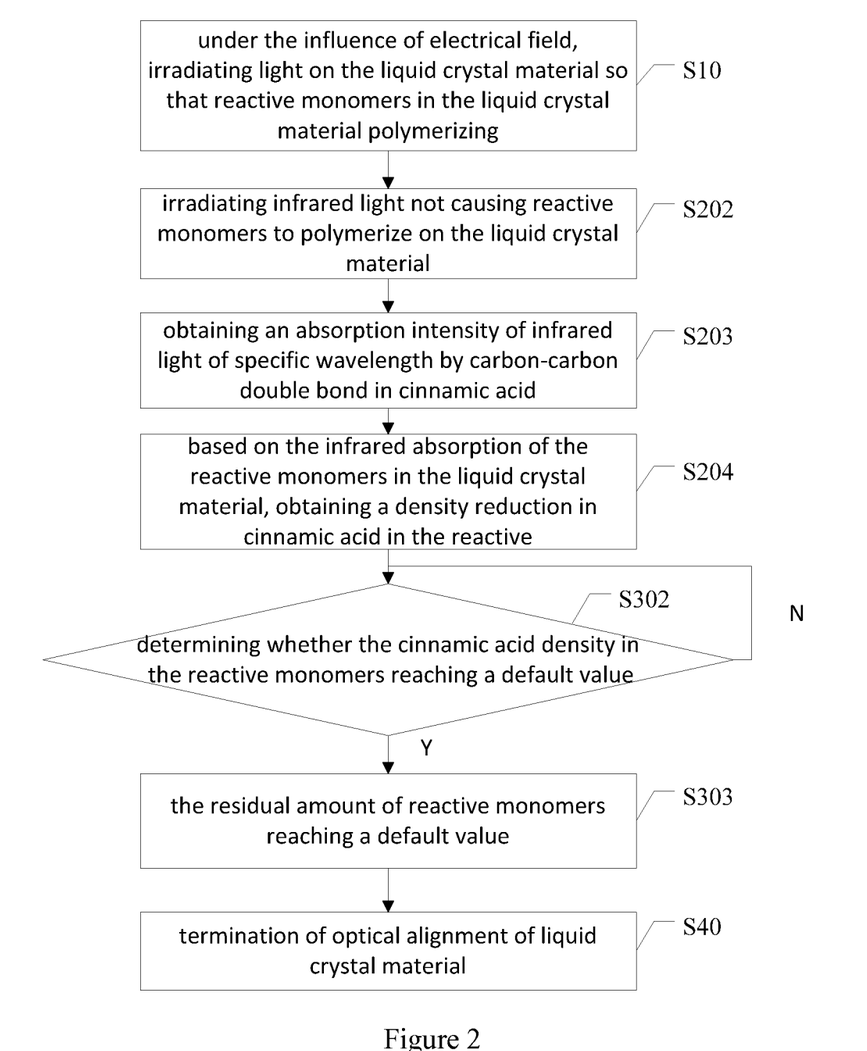
FIG. 2 is a specific flowchart showing the first embodiment of the method for termination detection of optical alignment of liquid crystal material according to the present invention.
Figure 3:
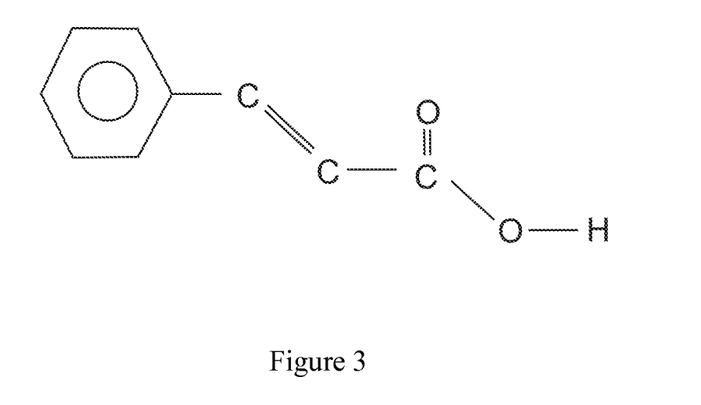
FIG. 3 is a schematic view showing the molecular structure of the cinnamic acid in the first embodiment of the method for termination detection of optical alignment of liquid crystal material according to the present invention.

Referring to FIGS. 1-3, FIGS. 1-3 show the first embodiment of a method for termination detection of optical alignment of liquid crystal material according to the present invention.

The method for termination detection of optical alignment of liquid crystal material in the instant embodiment is applied to PSVA technique. As shown in FIG. 1, the method for termination detection of optical alignment of liquid crystal material comprises the following steps:

Performing optical alignment on a liquid crystal material: which further comprises: under the influence of electrical field, irradiating light on the liquid crystal material so that reactive monomers in the liquid crystal material polymerizing.

Detecting a residual amount or a thickness change value of the reactive monomers in the liquid crystal material to determine the detected residual amount of the reactive monomers or a thickness change value in the liquid crystal box reaching a default value; when reaching the default value, terminating optical alignment of the liquid crystal material.

Step S10: performing optical alignment on a liquid crystal material. For example, the UV is used to align the liquid crystal. The UV passes the layers of glass substrate and the alignment film to reach the liquid crystal material to cause the reactive monomers in the liquid crystal material to polymerize.

Step S201: detecting a residual amount of the reactive monomers in the liquid crystal material. This step detects the residual amount of the reactive monomers in the liquid crystal material to prepare for the subsequent determination of optical alignment termination. Compared to the conventional control through controlling only the irradiation time for optical alignment management, this step overcomes the problem of potential under or over alignment.

Furthermore, as shown in FIG. 2, the step of detecting the residual amount of the reactive monomers in the liquid crystal material specifically comprises the following.

Step S202: irradiating infrared light on the liquid crystal material. The effect of the infrared irradiation is to: cause the reactive monomers to absorb the infrared to a certain extent to embody the step of detecting the residual amount of the reactive monomers in the liquid crystal material.

In addition, because the reactive monomers will not polymerize under the infrared irradiation, the detection can be performed throughout the entire reaction process. Based on the default specification, the reaction termination can be confirmed. In other words, the step only requires ensuring to irradiate infrared not causing reactive monomers to polymerize on the liquid crystal material.

Step S203: obtaining an absorption intensity of infrared light of specific wavelength by carbon-carbon double bond in cinnamic acid.

Step S204: based on the infrared absorption of the reactive monomers in the liquid crystal material, obtaining a density reduction in cinnamic acid in the reactive monomers.

The purpose of the above two steps is as follows. Because the cinnamic acid density in the reactive monomers will decrease after the above optical alignment reaction, the residual amount of the reactive monomers in the liquid crystal box can be computed by analyzing the absorption intensity of infrared light of specific wavelength by carbon-carbon double bond in cinnamic acid. In turn, the termination of the optical alignment reaction can be determined, wherein the molecular structure of the cinnamic acid is shown in FIG. 3.

Step S301: determining whether the detected residual amount of the reactive monomers reaching a default value; and when reaching the default value, a termination of optical alignment of the liquid crystal material is determined. The step comprises the following:

Step S302: determining whether the cinnamic acid density in the reactive monomers reaching a default value. When the cinnamic acid density in the reactive monomers reaching a default value, the residual amount of the reactive monomers in the liquid crystal material also reaches a default value, and step S40 is taken to terminate the alignment to avoid an over alignment. When the cinnamic acid density in the reactive monomers reaching a default value, the residual amount of the reactive monomers in the liquid crystal material has not reached a default value yet. Therefore, the alignment must continue to avoid under alignment. Then, the process proceeds to the determination step.

Figure 4:
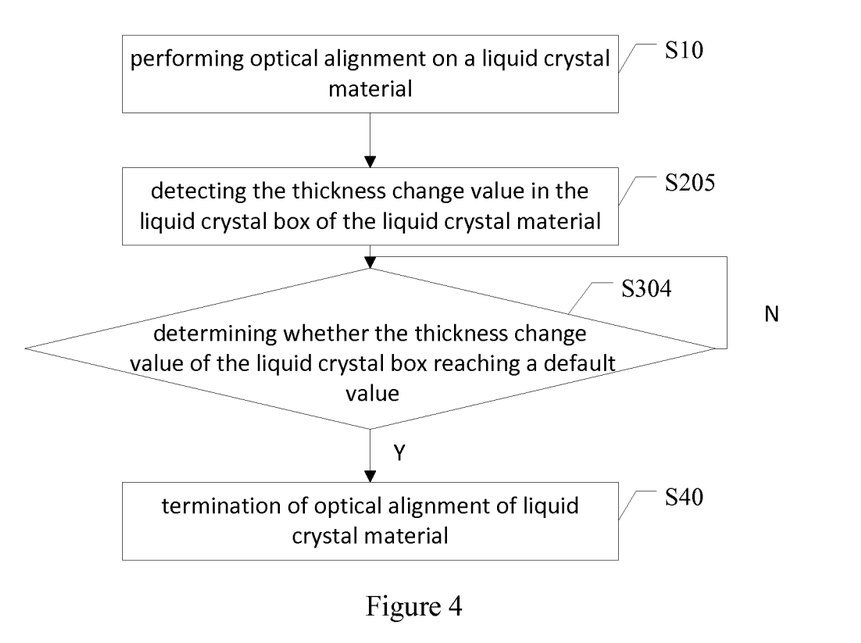
FIG. 4 is a flowchart showing the second embodiment of the method for termination detection of optical alignment of liquid crystal material according to the present invention.

Referring to FIG. 4, FIG. 4 is a flowchart showing the second embodiment of the method for termination detection of optical alignment of liquid crystal material according to the present invention.

The difference between the instant embodiment and the previous embodiment is that: the instant embodiment determining the alignment termination of the liquid crystal material based on the detected thickness change value in liquid crystal box.

The operating theory behind the instant embodiment is that the thickness of the liquid crystal box will reduce as the reactive monomers polymerize during the optical alignment reaction, the reaction progress of the optical alignment can be obtained by detecting the thickness of the liquid crystal box.

Step S205: detecting the thickness change value in the liquid crystal box of the liquid crystal material; the optical alignment reaction progress can be obtained through detecting the thickness change value in the liquid crystal box, which comprises: using an incident light not causing the monomers to polymerize on the liquid crystal box, such as, a visible light of wavelength 580 nm.

The present step prepares for the subsequent detecting thickness change of the liquid crystal box and determining optical alignment termination by irradiating on the liquid crystal box.

Step S304: determining whether the thickness change value of the liquid crystal box reaching a default value; and when reaching the default value, step S40 is taken to terminate the alignment to avoid an over alignment; otherwise, the alignment must continue to avoid under alignment. Then, the process proceeds to the determination step.

Figure 5:
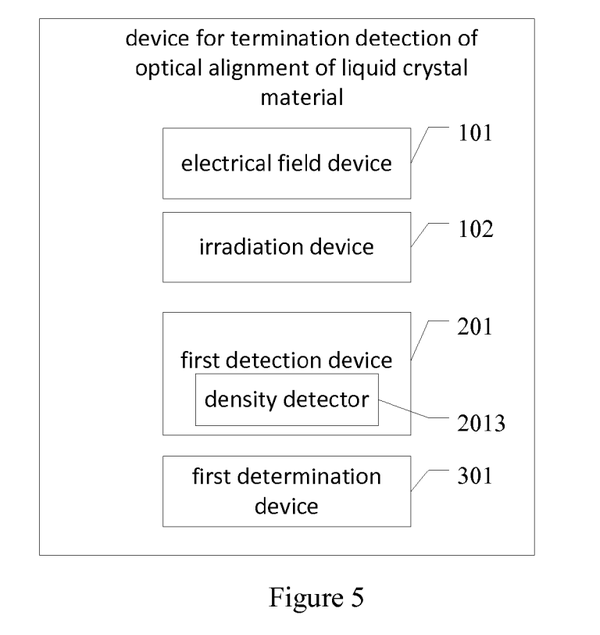
FIG. 5 is a schematic view showing the structure of the first embodiment of the device for termination detection of optical alignment of liquid crystal material according to the present invention.
Figure 6:
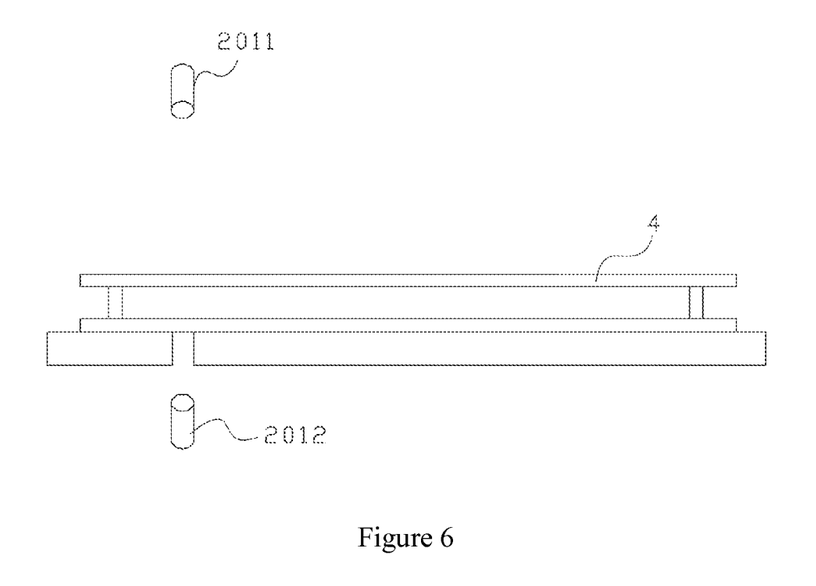
FIG. 6 is a schematic view showing the structure of detecting the residual amount of the reactive monomers in the first embodiment of the device for termination detection of optical alignment of liquid crystal material according to the present invention.

The present invention further discloses a device for termination detection of optical alignment of liquid crystal material. Referring to FIGS. 5-6, FIGS. 5-6 show a first embodiment of the device for termination detection of optical alignment of liquid crystal material of the present invention.

As shown in FIG. 5, the device for termination detection of optical alignment of liquid crystal material at least comprises: an electrical field device 101 for generating an electrical field; an irradiation device 102 for irradiating light so as to cause reactive monomers in a liquid crystal material to polymerize under the influence of electrical field and the irradiating light to realize optical alignment of liquid crystal material; a first detection device 201 for detecting a residual amount of reactive monomers in the liquid crystal material; and a first determination device 301 for determining whether the detected residual amount of reactive monomers in the liquid crystal material reaching a default value; wherein when the first determination device 301 determining the default value being reached, terminating the optical alignment on the liquid crystal material.

As shown in FIG. 6, the first detection device 201 at least comprises: an infrared transmission probe 2011, disposed at top of a liquid crystal box 4 containing the liquid crystal material to irradiate infrared light on the liquid crystal box 4; an infrared receiving probe 2012, disposed at bottom of the liquid crystal box 4 containing the liquid crystal material to receive infrared light on the liquid crystal box 4; and a density detector 2013, based on conditions of the infrared transmission probe 2011 irradiating infrared light and the infrared receiving probe 2012 receiving infrared light, for obtaining the infrared absorption intensity by the reactive monomers in the liquid crystal box 4 and determining a reduction in a density of cinnamic acid in the reactive monomers.

The purpose of the infrared transmission probe 2011 and infrared receiving probe 2012 is: to allow the reactive monomers to absorb infrared light so as to embody the detection of the residual amount of the reactive monomers in the liquid crystal material.

In addition, because the reactive monomers will not polymerize under the infrared irradiation, the detection can be performed throughout the entire reaction process.

The purpose of the density detector 2013 is as follows. Because the cinnamic acid density in the reactive monomers will decrease after the above optical alignment reaction, the density detector 2013 can compute the residual amount of the reactive monomers in the liquid crystal box by analyzing the absorption intensity of infrared light of specific wavelength by carbon-carbon double bond in cinnamic acid. In turn, the termination of the optical alignment reaction can be determined by the first determination device 301.

In actual practice, the first determination device 301 determines whether the cinnamic acid density in the reactive monomers decreased to a default value. When the cinnamic acid density in the reactive monomers is decreased to a default value, the residual amount of the reactive monomers in the liquid crystal material also is decreased a default value, then the termination is taken to terminate the alignment to avoid an over alignment. When the first determination device 301 determines the cinnamic acid density in the reactive monomers not yet decreased to a default value, the residual amount of the reactive monomers in the liquid crystal material has not decreased to a default value yet. Correspondingly, the alignment must continue to avoid under alignment.

Figure 7:
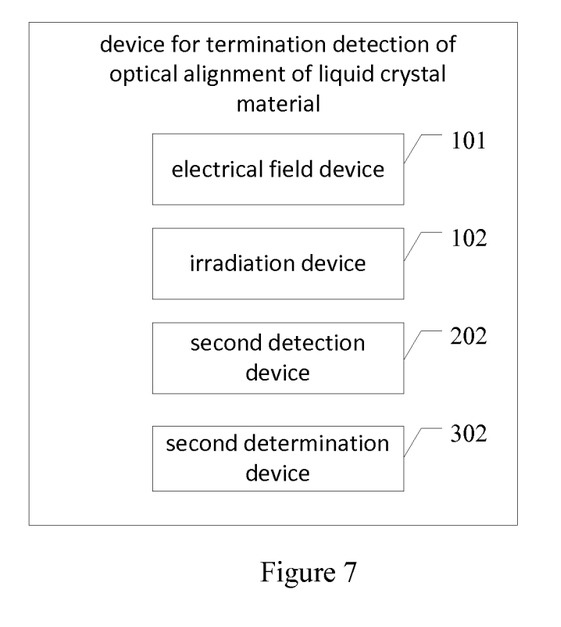
FIG. 7 is a schematic view showing the structure of the second embodiment of the device for termination detection of optical alignment of liquid crystal material according to the present invention.
Figure 8:
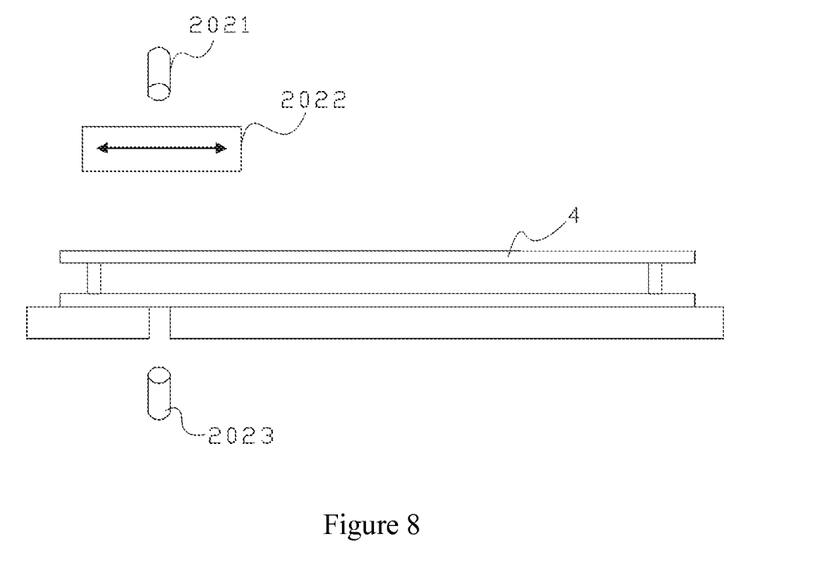
FIG. 8 is a schematic view showing the structure of detecting the thickness change in the liquid crystal box in the second embodiment of the device for termination detection of optical alignment of liquid crystal material according to the present invention.

Referring to FIGS. 7-8, FIGS. 7-8 show a second embodiment of the device for termination detection of optical alignment of liquid crystal material of the present invention.

As shown in FIG. 7, the device for termination detection of optical alignment of liquid crystal material of the present invention at least comprises: an electrical field device 101 for generating an electrical field; an irradiation device 102 for irradiating light so as to cause reactive monomers in a liquid crystal material to polymerize under the influence of electrical field and the irradiating light to realize optical alignment of liquid crystal material; a second detection device 202 for detecting a thickness change value in a liquid crystal box of the liquid crystal material; and a second determination device 302 for determining whether the detected thickness change value in the liquid crystal box reaching a default value; wherein when the second determination device 302 determining the default value being reached, terminating the optical alignment on the liquid crystal material.

The operating theory behind the instant embodiment is that the thickness of the liquid crystal box will reduce as the reactive monomers polymerize during the optical alignment reaction, the reaction progress of the optical alignment can be obtained by detecting the thickness of the liquid crystal box.

As shown in FIG. 8, the second detection device 202 at least comprises: a light source 2021, for generating an incident light not causing the reactive monomers to polymerize to irradiate on the liquid crystal box 4, for example, a visible light of wavelength 580 nm.

In a preferred embodiment of the present invention, the second detection device further comprises: a polarizer 2022 disposed at the top of the liquid crystal box, and an analyzer 2023 disposed at the bottom of the liquid crystal box 4. The polarizer 2022 and the analyzer 2023 collaborate to detect the thickness change value in the liquid crystal box. Through detecting the thickness change in the liquid crystal box, the reaction progress of optical alignment can be obtained.

In actual practice, the polarizer 2022 and the analyzer 2023 detect the thickness change in the liquid crystal box to prepare for subsequent determination of the termination of optical alignment of liquid crystal material. The second determination device 302 determines whether the thickness change value in the liquid crystal box reaching a default value. When the thickness change value in the liquid crystal box reaching a default value, the termination is taken to terminate the alignment to avoid an over alignment. When the second determination device 302 determines the thickness change value in the liquid crystal box reaching a default value, the alignment must continue to avoid under alignment.

Through detecting the residual amount of the reactive monomers or the thickness change in liquid crystal box, the present invention can determine the termination of the optical alignment on the liquid crystal material. As such, the present invention can realize the automatic control of the irradiation time in optical alignment to reduce the effect of individual glass substrate variation on the optical alignment to avoid affecting the reaction process of alignment on reactive monomer.

Embodiments of the present invention have been described, but not intending to impose any unduly constraint to the appended claims. Any modification of equivalent structure or equivalent process made according to the disclosure and drawings of the present invention, or any application thereof, directly or indirectly, to other related fields of technique, is considered encompassed in the scope of protection defined by the claims of the present invention.

What is claimed is:

1. A method for termination detection of optical alignment of liquid crystal material, which comprises:
   performing optical alignment on a liquid crystal material, which further comprising: under the influence of electrical field, irradiating light on the liquid crystal material so that reactive monomers in the liquid crystal material polymerizing;
   detecting a residual amount or a thickness change value of the reactive monomers in the liquid crystal material to determine the detected residual amount of the reactive monomers or thickness change value in the liquid crystal box reaching a default value; when reaching the default value, terminating optical alignment of the liquid crystal material.

2. The method for termination detection of optical alignment of liquid crystal material as claimed in claim 1, characterized in that the step of detecting a residual amount of the reactive monomers in the liquid crystal material further comprises:
   irradiating infrared light on the liquid crystal material; and
   based on the infrared absorption of the reactive monomers in the liquid crystal material, obtaining a density reduction in cinnamic acid in the reactive monomers.

3. The method for termination detection of optical alignment of liquid crystal material as claimed in claim 2, characterized in that the step of irradiating infrared light on the liquid crystal material further comprises:
   irradiating infrared light that will not cause the reactive monomers to polymerize on the liquid crystal material.

4. The method for termination detection of optical alignment of liquid crystal material as claimed in claim 2, characterized in that the step of based on the infrared absorption of the reactive monomers in the liquid crystal material, obtaining a density reduction in cinnamic acid in the reactive monomers further comprises:
   obtaining an absorption intensity of infrared light of specific wavelength by carbon-carbon double bond in cinnamic acid.

5. The method for termination detection of optical alignment of liquid crystal material as claimed in claim 4, characterized in that the step of irradiating infrared light on the liquid crystal material further comprises:
   irradiating infrared light that will not cause the reactive monomers to polymerize on the liquid crystal material.

6. The method for termination detection of optical alignment of liquid crystal material as claimed in claim 1, characterized in that the step of detecting a thickness change value in the liquid crystal box further comprises:
   irradiating an incident light that will not cause the reactive monomers to polymerize on the liquid crystal material.

7. The method for termination detection of optical alignment of liquid crystal material as claimed in claim 6, characterized in that the incident light has a wavelength of 580 nm.

8. A device for termination detection of optical alignment of liquid crystal material, which at least comprises:
- an electrical field device for generating an electrical field;
- an irradiation device for irradiating light so as to cause reactive monomers in a liquid crystal material to polymerize under the influence of electrical field and the irradiating light to realize optical alignment of liquid crystal material;
- a first detection device for detecting a residual amount of reactive monomers in the liquid crystal material; and
- a first determination device for determining whether the detected residual amount of reactive monomers in the liquid crystal material reaching a default value; wherein when the first determination device determining the default value being reached, terminating the optical alignment on the liquid crystal material.

9. The device for termination detection of optical alignment of liquid crystal material as claimed in claim 8, characterized in that the first detection device at least comprises:
- an infrared transmission probe, disposed at top of a box containing the liquid crystal material to irradiate infrared light on the liquid crystal box;
- an infrared receiving probe, disposed at bottom of the box containing the liquid crystal material to receive infrared light on the liquid crystal box; and
- a density detector, based on conditions of the infrared transmission probe irradiating infrared light and the infrared receiving probe receiving infrared light, for obtaining the infrared absorption intensity by the reactive monomers in the liquid crystal box and determining a reduction in a density of cinnamic acid in the reactive monomers.

10. The device for termination detection of optical alignment of liquid crystal material as claimed in claim 9, characterized in that the infrared transmission probe irradiates an infrared light that will not cause the reactive monomers to polymerize on the liquid crystal material.

11. The device for termination detection of optical alignment of liquid crystal material as claimed in claim 9, characterized in that the density detector, through obtaining an absorption intensity of infrared light of specific wavelength by carbon-carbon double bond in cinnamic acid, computes the residual amount of reactive monomers in the liquid crystal box.

12. The device for termination detection of optical alignment of liquid crystal material as claimed in claim 11, characterized in that the infrared transmission probe irradiates an infrared light that will not cause the reactive monomers to polymerize on the liquid crystal material.

13. A device for termination detection of optical alignment of liquid crystal material, which at least comprises:
- an electrical field device for generating an electrical field;
- an irradiation device for irradiating light so as to cause reactive monomers in a liquid crystal material to polymerize under the influence of electrical field and the irradiating light to realize optical alignment of liquid crystal material;
- a second detection device for detecting a thickness change value in a liquid crystal box of the liquid crystal material; and
- a second determination device for determining whether the detected thickness change value in the liquid crystal box reaching a default value; wherein when the second determination device determining the default value being reached, terminating the optical alignment on the liquid crystal material.

14. The device for termination detection of optical alignment of liquid crystal material as claimed in claim 13, characterized in that the second detection device at least comprises:
- a light source, for generating an incident light not causing the reactive monomers to polymerize to irradiate on the liquid crystal box.

15. The device for termination detection of optical alignment of liquid crystal material as claimed in claim 14, characterized in that the light source uses a visible light of wavelength 580 nm.

16. The device for termination detection of optical alignment of liquid crystal material as claimed in claim 14, characterized in that the second detection device further comprises:
- a polarizer disposed at the top of the liquid crystal box.

17. The device for termination detection of optical alignment of liquid crystal material as claimed in claim 14, characterized in that the second detection device further comprises:
- an analyzer disposed at the bottom of the liquid crystal box.

* * * * *